(12) United States Patent
Ladet

(10) Patent No.: US 10,143,471 B2
(45) Date of Patent: Dec. 4, 2018

(54) SURGICAL FASTENERS AND METHODS FOR SEALING WOUNDS

(71) Applicant: Sofradim Production, Trévoux (FR)

(72) Inventor: Sébastien Ladet, Caluire & Cuire (FR)

(73) Assignee: Sofradim Production, Trevoux (FR)

( * ) Notice: Subject to any disclaimer, the term of this patent is extended or adjusted under 35 U.S.C. 154(b) by 279 days.

(21) Appl. No.: 15/048,284

(22) Filed: Feb. 19, 2016

(65) Prior Publication Data

US 2016/0166251 A1    Jun. 16, 2016

Related U.S. Application Data

(62) Division of application No. 13/070,598, filed on Mar. 24, 2011, now Pat. No. 9,272,074.

(60) Provisional application No. 61/317,433, filed on Mar. 25, 2010.

(51) Int. Cl.
| | | |
|---|---|---|
| A61B 17/00 | (2006.01) | |
| A61B 17/064 | (2006.01) | |
| A61L 31/04 | (2006.01) | |
| A61L 31/08 | (2006.01) | |
| A61L 31/10 | (2006.01) | |
| A61B 17/122 | (2006.01) | |
| A61L 31/16 | (2006.01) | |

(52) U.S. Cl.
CPC ........ *A61B 17/0644* (2013.01); *A61B 17/064* (2013.01); *A61B 17/122* (2013.01); *A61L 31/04* (2013.01); *A61L 31/08* (2013.01); *A61L 31/10* (2013.01); *A61L 31/16* (2013.01); *A61B 2017/00884* (2013.01)

(58) Field of Classification Search
CPC .......... A61L 31/04; A61L 31/08; A61L 31/10; A61B 17/064
USPC ........... 606/151, 213, 214; 424/135.1, 178.1, 424/400, 422, 423, 443, 487
See application file for complete search history.

(56) References Cited

U.S. PATENT DOCUMENTS

| | | |
|---|---|---|
| 3,767,085 A | 10/1973 | Cannon et al. |
| 4,326,532 A | 4/1982 | Hammar |
| 4,359,049 A | 11/1982 | Redl et al. |

(Continued)

FOREIGN PATENT DOCUMENTS

| | | |
|---|---|---|
| BE | 1008260 A6 | 2/1996 |
| EP | 0490854 A2 | 6/1992 |

(Continued)

OTHER PUBLICATIONS

Q Shi, et al., "The Immobilization of Proteins on Biodegradable Polymer Fibers via Click Chemistry", Biomaterials, 29, (2008), pp. 1118-1126.

(Continued)

*Primary Examiner* — Vy Bui

(57) ABSTRACT

A method for closing a wound in tissue is provided which includes providing a surgical fastener having a plurality of reactive members of a specific binding pair attached on a surface of the surgical fastener, and providing tissue with a plurality of complementary reactive members of the specific binding pair, wherein upon contact of the reactive members on the surface of the surgical fastener with the complimentary reactive members on the tissue, covalent bonds are formed between the reactive members and the complementary reactive members, thus adhering the device to the tissue.

22 Claims, 2 Drawing Sheets

(56) References Cited

U.S. PATENT DOCUMENTS

| | | |
|---|---|---|
| 4,464,321 A | 8/1984 | Pittalis et al. |
| 4,538,920 A | 9/1985 | Drake |
| 4,753,536 A | 6/1988 | Spehar et al. |
| 4,839,345 A | 6/1989 | Doi et al. |
| 4,857,403 A | 8/1989 | De Lucca et al. |
| 4,880,662 A | 11/1989 | Habrich et al. |
| 5,021,207 A | 6/1991 | De Lucca et al. |
| 5,372,585 A | 12/1994 | Tiefenbrun et al. |
| 5,455,308 A | 10/1995 | Bastiaansen |
| 5,562,946 A | 10/1996 | Fofonoff et al. |
| 5,578,662 A | 11/1996 | Bennett et al. |
| 5,582,955 A | 12/1996 | Keana et al. |
| 5,612,050 A | 3/1997 | Rowe et al. |
| 5,804,318 A | 9/1998 | Pinchuk et al. |
| 5,911,942 A | 6/1999 | Fofonoff et al. |
| 6,107,365 A | 8/2000 | Bertozzi et al. |
| 6,107,453 A | 8/2000 | Zuccato et al. |
| 6,312,725 B1 | 11/2001 | Wallace et al. |
| 6,342,591 B1 | 1/2002 | Zamora et al. |
| 6,451,032 B1 | 9/2002 | Ory et al. |
| 6,534,611 B1 | 3/2003 | Darling et al. |
| 6,552,103 B1 | 4/2003 | Bertozzi et al. |
| 6,570,040 B2 | 5/2003 | Saxon et al. |
| 6,576,000 B2 | 6/2003 | Carrison |
| 6,624,245 B2 | 9/2003 | Wallace et al. |
| 6,881,766 B2 | 4/2005 | Hain |
| 7,012,126 B2 | 3/2006 | Matsuda et al. |
| 7,105,629 B2 | 9/2006 | Matsuda et al. |
| 7,122,703 B2 | 10/2006 | Saxon et al. |
| 7,144,976 B2 | 12/2006 | Matsuda et al. |
| 7,172,877 B2 | 2/2007 | Ting |
| 7,247,692 B2 | 7/2007 | Laredo |
| 7,294,357 B2 | 11/2007 | Roby |
| 7,371,719 B2 | 5/2008 | Stupp et al. |
| 7,375,234 B2 | 5/2008 | Sharpless et al. |
| 7,560,588 B2 | 7/2009 | Breitenkamp et al. |
| 7,618,944 B2 | 11/2009 | Breitenkamp et al. |
| 7,638,558 B2 | 12/2009 | Breitenkamp et al. |
| 7,667,012 B2 | 2/2010 | Saxon et al. |
| 7,795,355 B2 | 9/2010 | Matyjaszewski et al. |
| 7,807,619 B2 | 10/2010 | Bertozzi et al. |
| 7,901,704 B2 | 3/2011 | Richard |
| 7,981,444 B2 | 7/2011 | Tomalia et al. |
| 7,985,424 B2 | 7/2011 | Tomalia et al. |
| 8,034,396 B2 | 10/2011 | Kapiamba et al. |
| 8,512,728 B2 | 8/2013 | Ladet et al. |
| 8,535,477 B2 * | 9/2013 | Ladet ............... A61L 15/22 156/325 |
| 8,968,818 B2 | 3/2015 | Belcheva et al. |
| 9,272,074 B2 | 3/2016 | Ladet |
| 2002/0016003 A1 | 2/2002 | Saxon et al. |
| 2002/0161170 A1 | 10/2002 | Matsuda et al. |
| 2002/0169275 A1 | 11/2002 | Matsuda et al. |
| 2002/0173616 A1 | 11/2002 | Matsuda et al. |
| 2003/0100086 A1 | 5/2003 | Yao et al. |
| 2003/0135238 A1 | 7/2003 | Milbocker |
| 2003/0162903 A1 | 8/2003 | Day |
| 2003/0199084 A1 | 10/2003 | Saxon et al. |
| 2003/0205454 A1 | 11/2003 | Hlavinka et al. |
| 2004/0170752 A1 | 9/2004 | Luthra et al. |
| 2004/0185053 A1 | 9/2004 | Govindan |
| 2004/0209317 A1 | 10/2004 | Ting |
| 2005/0038472 A1 | 2/2005 | Furst |
| 2005/0148032 A1 | 7/2005 | Saxon et al. |
| 2005/0222427 A1 | 10/2005 | Sharpless et al. |
| 2005/0233389 A1 | 10/2005 | Ting et al. |
| 2006/0018948 A1 | 1/2006 | Guire et al. |
| 2006/0036022 A1 | 2/2006 | Callaghan et al. |
| 2006/0085033 A1 | 4/2006 | Criscuolo et al. |
| 2006/0108393 A1 | 5/2006 | Heinrich et al. |
| 2006/0110782 A1 | 5/2006 | Bertozzi et al. |
| 2006/0147963 A1 | 7/2006 | Barone et al. |
| 2006/0193865 A1 | 8/2006 | Govindan |
| 2006/0228300 A1 | 10/2006 | Chang et al. |
| 2006/0228357 A1 | 10/2006 | Chang et al. |
| 2006/0240092 A1 | 10/2006 | Breitenkamp et al. |
| 2006/0276658 A1 | 12/2006 | Saxon et al. |
| 2007/0020620 A1 | 1/2007 | Finn et al. |
| 2007/0037964 A1 | 2/2007 | Saxon et al. |
| 2007/0060658 A1 | 3/2007 | Diaz et al. |
| 2007/0077564 A1 | 4/2007 | Roitman et al. |
| 2007/0086942 A1 | 4/2007 | Chang et al. |
| 2007/0087001 A1 | 4/2007 | Taylor et al. |
| 2007/0099251 A1 | 5/2007 | Zhang et al. |
| 2007/0140966 A1 | 6/2007 | Chang et al. |
| 2007/0178133 A1 | 8/2007 | Rolland |
| 2007/0178448 A1 | 8/2007 | Tsao et al. |
| 2007/0190597 A1 | 8/2007 | Agnew et al. |
| 2007/0244265 A1 | 10/2007 | Matyjaszewski et al. |
| 2007/0244296 A1 | 10/2007 | Tomalia et al. |
| 2007/0249014 A1 | 10/2007 | Agnew et al. |
| 2007/0254006 A1 | 11/2007 | Loose et al. |
| 2007/0258889 A1 | 11/2007 | Douglas et al. |
| 2007/0269369 A1 | 11/2007 | Gegg et al. |
| 2007/0272122 A1 | 11/2007 | Lahann et al. |
| 2007/0275387 A1 | 11/2007 | Ju |
| 2007/0298006 A1 | 12/2007 | Tomalia et al. |
| 2008/0015138 A1 | 1/2008 | Hamilton et al. |
| 2008/0035243 A1 | 2/2008 | Breitenkamp et al. |
| 2008/0038472 A1 | 2/2008 | Suzuki et al. |
| 2008/0045686 A1 | 2/2008 | Meagher et al. |
| 2008/0050731 A1 | 2/2008 | Agnew et al. |
| 2008/0051562 A1 | 2/2008 | Chaikof et al. |
| 2008/0121657 A1 | 5/2008 | Voegele et al. |
| 2008/0138317 A1 | 6/2008 | Fung |
| 2008/0160017 A1 | 7/2008 | Baker et al. |
| 2008/0166363 A1 | 7/2008 | Govindan et al. |
| 2008/0171067 A1 | 7/2008 | Govindan et al. |
| 2008/0187956 A1 | 8/2008 | Carrico et al. |
| 2008/0199736 A1 | 8/2008 | Gadeken et al. |
| 2008/0200628 A1 | 8/2008 | Gadeken et al. |
| 2008/0207913 A1 | 8/2008 | Breitenkamp et al. |
| 2008/0214436 A1 | 9/2008 | Yu et al. |
| 2008/0214801 A1 | 9/2008 | Saxon et al. |
| 2008/0214831 A1 | 9/2008 | Sharpless et al. |
| 2008/0221043 A1 | 9/2008 | Harth et al. |
| 2008/0241856 A1 | 10/2008 | Wong et al. |
| 2008/0241892 A1 | 10/2008 | Roitman et al. |
| 2008/0242171 A1 | 10/2008 | Huang et al. |
| 2008/0248126 A1 | 10/2008 | Cheng et al. |
| 2008/0267878 A1 | 10/2008 | Robillard et al. |
| 2008/0283572 A1 | 11/2008 | Boyden et al. |
| 2008/0311412 A1 | 12/2008 | Fokin et al. |
| 2008/0317861 A1 | 12/2008 | Guan |
| 2009/0012457 A1 | 1/2009 | Childers et al. |
| 2009/0018646 A1 | 1/2009 | Zhao |
| 2009/0027603 A1 | 1/2009 | Samulski et al. |
| 2009/0053139 A1 | 2/2009 | Shi et al. |
| 2009/0054619 A1 | 2/2009 | Baker et al. |
| 2009/0061010 A1 | 3/2009 | Zale et al. |
| 2009/0069561 A1 | 3/2009 | Fokin et al. |
| 2009/0082224 A1 | 3/2009 | Haddleton et al. |
| 2009/0099108 A1 | 4/2009 | Jones |
| 2009/0124534 A1 | 5/2009 | Reineke |
| 2009/0137424 A1 | 5/2009 | Tsao et al. |
| 2009/0181402 A1 | 7/2009 | Finn et al. |
| 2009/0182151 A1 | 7/2009 | Wu et al. |
| 2009/0202433 A1 | 8/2009 | Chang et al. |
| 2009/0203131 A1 | 8/2009 | Reineke et al. |
| 2009/0214755 A1 | 8/2009 | Armani et al. |
| 2009/0220607 A1 | 9/2009 | Kiser et al. |
| 2009/0240030 A1 | 9/2009 | Ju et al. |
| 2009/0247651 A1 | 10/2009 | Kapiamba et al. |
| 2009/0250588 A1 | 10/2009 | Robeson et al. |
| 2009/0253609 A1 | 10/2009 | Fleury et al. |
| 2009/0259016 A1 | 10/2009 | Johnson et al. |
| 2009/0263468 A1 | 10/2009 | McAnulty et al. |
| 2009/0269277 A1 | 10/2009 | Chang et al. |
| 2009/0281250 A1 | 11/2009 | DeSimone et al. |
| 2009/0297609 A1 | 12/2009 | Shoichet et al. |
| 2009/0306310 A1 | 12/2009 | Wu et al. |
| 2009/0312363 A1 | 12/2009 | Bradner et al. |
| 2009/0325292 A1 | 12/2009 | Baker et al. |
| 2010/0011472 A1 | 1/2010 | Hugel et al. |

(56) References Cited

U.S. PATENT DOCUMENTS

| | | | |
|---|---|---|---|
| 2010/0015046 | A1 | 1/2010 | Govindan et al. |
| 2010/0021391 | A1 | 1/2010 | Douglas et al. |
| 2010/0034862 | A1 | 2/2010 | Laronde et al. |
| 2010/0047258 | A1 | 2/2010 | Wang et al. |
| 2010/0048738 | A1 | 2/2010 | Fleury et al. |
| 2010/0069578 | A1 | 3/2010 | Faust et al. |
| 2010/0098640 | A1 | 4/2010 | Cohen et al. |
| 2010/0104589 | A1 | 4/2010 | Govindan et al. |
| 2010/0121022 | A1 | 5/2010 | Musa et al. |
| 2010/0159508 | A1 | 6/2010 | Yang et al. |
| 2010/0212829 | A1* | 8/2010 | Ladet ............... A61L 15/22 156/325 |
| 2010/0215659 | A1 | 8/2010 | Ladet |
| 2010/0215748 | A1 | 8/2010 | Ladet et al. |
| 2010/0247433 | A1 | 9/2010 | Tirrell et al. |
| 2010/0286405 | A1 | 11/2010 | Fokin et al. |
| 2010/0291171 | A1 | 11/2010 | Crescenzi et al. |
| 2010/0303754 | A1 | 12/2010 | Turpin et al. |
| 2011/0008251 | A1 | 1/2011 | Chang et al. |
| 2011/0052696 | A1 | 3/2011 | Hult et al. |
| 2011/0060107 | A1 | 3/2011 | Matyjaszewski et al. |
| 2011/0143435 | A1 | 6/2011 | Stayton et al. |
| 2011/0177156 | A1 | 7/2011 | Szoka, Jr. et al. |
| 2011/0183417 | A1 | 7/2011 | Reineke |
| 2011/0213123 | A1 | 9/2011 | Bertozzi et al. |

FOREIGN PATENT DOCUMENTS

| | | |
|---|---|---|
| EP | 1790702 A1 | 5/2007 |
| EP | 1795563 A1 | 6/2007 |
| EP | 1975230 A1 | 10/2008 |
| EP | 2014308 A2 | 1/2009 |
| EP | 2090592 A1 | 8/2009 |
| WO | 9910019 A2 | 3/1999 |
| WO | 2006012569 A1 | 2/2006 |
| WO | 2007041394 A2 | 4/2007 |
| WO | 2007121055 A1 | 10/2007 |
| WO | 2008013618 A1 | 1/2008 |
| WO | 2008075955 A2 | 6/2008 |
| WO | 2008077406 A2 | 7/2008 |
| WO | 2008108736 A1 | 9/2008 |
| WO | 2008115694 A2 | 9/2008 |
| WO | 2008120016 A1 | 10/2008 |
| WO | 2010095049 A1 | 8/2010 |

OTHER PUBLICATIONS

Jerome, et al., "Recent Advances in the Synthesis of Aliphatic Polyesters Ring-Opening Polymerization", Advanced Drug Delivery Reviews, 60, (2008), pp. 1056-1076.

Zhang, et al., "2-Azido-2-deoxycellulose: Synthesis and 1, 3-Dipolar Cycloaddition", Helvetica Chimica Acta, vol. 91, pp. 608-617 (2008).

R. Riva, et al., "Contribution of "Click Chemistry" to the Synthesis of Antimicrobial Aliphatic Copolyester", Polymer 49, (2008), pp. 2023-2028.

Baskin, et al., "Copper Free Click Chemistry for Dynamic In Vivo Imaging", PNAS, vol. 104, No. 43, (Oct. 23, 2007), pp. 16793-16797.

Codelli, et al., "Second Generation Difluorinated Cyclooctynes for Copper-Free Click Chemistry", J. Am. Chem. Soc., vol. 130, No. 34, (2008), pp. 11486-11493.

Sletten and Bertozzi, "A Hydrophilic Azacyclooctyne for Cu-free Click Chemistry", Org. Lett. (2008) 10(14), pp. 3097-3099.

Cazalis, et al., "C-Terminal Site-Specific PEGylation of a Truncated Thrombomodulin Mutant with Retention of Full Bioactivity", Bioconjugate Chem., (2004), 15, pp. 1005-1009.

Haridas, et al., "Design and Synthesis of Triazole-based Peptidedendrimers" Tetrahedron Letters, vol. 48, (2007), pp. 4719-4722.

Raghavan, et al., "Chemical Probes for Profiling Fatty Acid-associated Proteins in Living Cells", Bioorg. Med. Chem. Lett., 18 (2008), pp. 5982-5986.

LeDevedec, et al., "Separation of Chitosan Oligomers by Immobilized Metal Affinity Chromatography", Journal of Chromatography A., 2008, 1194(2), pp. 165-171.

Hartgerink, et al., "Peptide-amphiphile Nanofibers: A Versatile Scaffold for the Preparation of Self Assembling Materials", PNAS, 2002; 99(2), pp. 5133-5138.

Van Berkel, et al., "Metal-Free Triazole Formation as a Tool for Bioconjugation" Chem Bio Chem, 8, (2007), pp. 1504-1508.

Nottelet, et al., Synthesis of an X-ray opaque biodegradable copolyester by chemical modification of poly (.epsilon.-caprolactone) Biomaterials, 27, (2006), pp. 4943-4954.

Smith, et al., "Synthesis and Convenient Functionalization of Azide-labeled Diacyglycerol Analogues for Modular Access to Biologically Active Lipid Probes", Bioconjugate Chem, 19(9), (2008). pp. 1855-1863.

Skierka, et al., "The Influence of Different Acids and Pepsin on the Extractability of Collagen From the Skin of Baltic Cod (*Gadus morhua*)", Food Chemisty, 105, (2007), pp. 1302-1306.

Eastoe, "The Amino Acid Composition of Mammalian Collagen and Gelatin", vol. 61, (1955), pp. 589-600.

Sicherl, et al., "Orthogonally Protected Sugar Diamino Acids as Building Blocks for Linear and Branched Oligosaccharide Mimetics", Angew. Chem. Int. Ed. 44, (2005), pp. 2096-2099.

Laughlin, et al., "In Vivo Imaging of Membrane-Associated Glycans in Developing Zebrafish", Science, 320, (2008), pp. 664-667.

Worch and Wittmann, "Unexpected Formation of Complex Bridged Tetrazoles via Intramolecular 1,3-dipolar Cycloaddition of 1,2-0-cyanoalkylidene Derivatives of 3-azido-3-deoxy-D-allose", Carbohydrate Research, 343, (2008), pp. 2118-2129.

Witczak et al., "A Click Chemistry Approach to Glycomimetics: Michael addition of 2,3,4,6-tetra-O-acetyl-1-thio-.beta.-D-glucopyranose to 4-deoxy-1,2-O-isopropylident-L-glycero-pent-4-enopyranos-3-ulose—a convenient route to novel4-deoxy-(1.fwdarw.5)-5-C-thiodisaccharides", Carbohydrate Research, 342, (2007), 1929-1933.

Marra, et al., "Validation of the Copper(1)-Catalyzed Azide-Alkyne Coupling in Ionic Liquids, Synthesis of a Triazole-Linked C-Disaccharide as a Case Study", J. Org. Chem (2008), 73(6), pp. 2458-2461.

Srinivasachari, et al., "Versatile Supramolecular pDNA Vehicles via "Click Polymerization" of .beta.-cyclodextrin with oligoethyleneamines", Biomaterials, 30, (2009), pp. 928-938.

Arora, et al., "A Novel Domino-click Approach for the Synthesis of Sugar Based Unsymmetrical bis-1,2,3-triazoles", Carbohydrate Research, 343, (2008), 139-144.

Chen, et al., "Synthesis of a C.sub.3-symmetric (1.fwdarw.6)-N-acetyl-.beta.-D-glucosamine Octadecasaccharide using Click Chemistry", Carbohydrate Research, 340, (2005), pp. 2476-2482.

Gouin, et al., "Multi-Mannosides Based on a Carbohydrate Scaffold: Synthesis, Force Field Development, Molecular Dynamics Studies, and Binding Affinities for Lectin Con A", J. Org. Chem., 2007, 72(24), pp. 9032-9045.

Srinivasachari, etal., "Effects of Trehalose Click Polymer Length on pDNA Complex Stability and Delivery Efficacy", Biomaterials, 28, (2007), pp. 2885-2898.

Godeau, et al., Lipid-Conjugated Oligonucleotides via "Click Chemistry" Efficiently Inhibit Hepatitis C Virus Translation, J. med. Chem., 2008, 51(15), pp. 2374-4376.

Zou et al., "Cu-free Cycloaddition for Identifying Catalytic Active Adenylation Domains of Nonribosomal Peptide Synthesis by phage display", Bioorganic & Medicinal Chemistry Letters, 18 (2008), pp. 5664-5667.

Cantel, et al., "Synthesis and Conformational Analysis of a Cyclic Peptide Obtained via i to i+4 Intramolecular Side-chain to Side-chain Azide-Alkyne 1,3-Dipolar Cycloaddition" J. Org. Chem., 2008, 73 (15), pp. 5663-5614.

Dijk, et al., "Synthesis of Peptide-Based Polymers by Microwave-Assisted Cycloaddition Backbone Polymerization," Biomacro molecules, 2007, 8(2), pp. 327-330.

Koster, et al., "Spectroscopic and Electrochemical Studies of Ferroceryl Triazole Amino Acid and Peptide Bioconjugates Synthesized by Click Chemistry", Organometallics, 2008, 27(23) pp. 6326-6332.

(56) References Cited

OTHER PUBLICATIONS

Dijk, et al., "Synthesis and Characterization of Biodegradable Peptide-Baed Polymers Prepared by Microwave-Assisted Click Chemisty", Biomacromolecules, 2008, 9(10), pp. 2834-2843.

Jiang, et al., "Amphiphilic PEG/alkyl-grafted comb polylactides", J. Polymer Science Part B: Polymer Physics, 45(22), 2007, pp. 5227-5236.

Ochs, et al., "Low-Fouling, Biofunctionalized, and Biodegradable Click Capsules", Biomacromolecules, 2008, 9(12), pp. 3389-3396.

Beatty and Tirrell, "Two-color Labeling of Temporally Defined Protein Populations in Mammalian Cells", Bioorg. Med. Chem. Lett., 18 (2008), pp. 5995-5999.

Kolb, et al., "Click Chemistry: Diverse Chemical Function from a Few Good Reactions", Angewandte Chemie, International Edition, Jun. 2001, pp. 2004-2021.

Krouit, et al., "Cellulose surface grafting with polycaprolactone by heterogeneous click-chemistry", European Polymer Journal 44, Dec. 2008, pp. 4074-4081.

Nandivada, et al. "Reactive polymer coatings that 'Click'.", Angewandte Chemie, International Edition 45, Apr. 2006, pp. 3360-3363.

Ossipov and Hilborn, Poly(vinyl alcohol)-Based Hydrogels Formed by "Click Chemistry", Macromelecules 2006, 39, pp. 1709-1718.

Binder and Sachsenhofer, "Click Chemistry in Polymer and Materials Science", Macromolecular Rapid Commun. 2007, 28, pp. 15-54.

International Preliminary Report on Patentability and Written Opinion of the International Searching Authority corresponding to International Application No. PCT/IB2011/001131, dated Sep. 25, 2012 (5 pages).

* cited by examiner

SURGICAL FASTENERS AND METHODS FOR SEALING WOUNDS

CROSS-REFERENCE TO RELATED APPLICATIONS

This application is a divisional of U.S. patent application Ser. No. 13/070,598 filed Mar. 24, 2011, which claims benefit of and priority to U.S. Provisional Application No. 61/317,433 filed Mar. 25, 2010, and the disclosures of each of the above-identified applications are hereby incorporated by reference in their entirety.

BACKGROUND

Technical Field

The present disclosure relates to methods of enhancing wound closure in tissue and, more particularly, the use of a surgical fastener having a plurality of reactive members of a specific binding pair, with a liquid precursor having a plurality of complementary reactive members of the specific binding pair, for sealing wounds in tissue.

Background of Related Art

Techniques for repairing damaged or diseased tissue are widespread in medicine. Wound closure devices such as sutures, staples, clips and other devices are frequently used to close wounds, whether created during the repair process or as a result of the damaged tissue. Even though these techniques are generally well suited to mechanically close a wound in any tissue, some of these techniques add small perforations to the wound tissue during the wound closing process. For example, lung tissue is extremely fragile and does not hold sutures well. That is to say, although sutures are strong enough to generally close a wound in lung tissue, suturing the lung tissue may result in small lung perforations because the lung tissue is so fragile. Such small perforations may allow for the leakage of bodily fluids post-operatively which can lead to post-operative complications, such as infection.

Surgical adhesives such as cyanoacrylates and fibrin glues have been used as fixatives in lieu of suturing or stapling the wound closed. However, these adhesives do not provide the necessary elasticity or mechanically strength often needed to keep the tissue wound closed.

Click chemistry is a popular term for reliable reactions that make it possible for certain chemical building blocks to "click" together and form an irreversible linkage. See, e.g., US Pub. No. 2005/0222427. Since its recent introduction, click chemistry has been used for ligation in biological and medical technology. In the case of azide-alkyne click chemistry, the reactions may be catalyzed or uncatalyzed. For example, copper-free click chemistry was recently developed by Bertozzi and colleagues using difluorinated cyclooctyne or DIFO. that reacts with azides rapidly at physiological temperatures without the need for a toxic catalyst. See. e.g. Baskin et al., Copper Free Click Chemistry for Dynamic In Vivo Imaging, PNAS, vol. 104, no. 43, 16793-16797 (Oct. 23, 2007). The critical reagent, a substituted cyclooctyne, possesses ring strain and electron-withdrawing fluorine substituents that together promote a [3+2] dipolar cycloaddition with azides. See also, US Pub. No. 2006/0110782 and Codelli et al., Second Generation Difluorinated Cyclooctynes for Copper-Free Click Chemistry, J. Am. Chem. Soc., vol. 130, no. 34, 11486-11493 (2008). Another suitable cyclooctyne is 6,7-dimethoxyaza-cyclooct-4-yne (DIMAC). See, Sletton and Bertozzi, A hydrophilic azacyclooctyne for Cu-free click chemistry, Org. Lett. (2008) 10 (14), 3097-3099. Other click chemistry reactions include Diels-Alder reactions, thiol-alkene reactions, and maleimide-thiol reactions. There is a continuing need to generate improvements in tissue repair technology and advance the state of the art.

SUMMARY

Methods for chemically bonding a surgical fastener to biological tissue in accordance with the present disclosure includes contacting a surgical fastener having a plurality of reactive members of a specific binding pair on a surface thereof with tissue having a plurality of complementary reactive members of the specific binding pair. Upon contact of the reactive members on the surface of the surgical fastener with the complimentary reactive members on the tissue, covalent bonds are formed between the reactive members and the complementary reactive members thereby bonding the fastener to the tissue.

In embodiments, the surgical fastener and the liquid precursor may be applied to biologic tissue to seal a wound. The liquid precursor may surface activate the tissue with reactive members which are complimentary to the reactive members positioned on the surface of the surgical fastener. The surgical fastener and the liquid precursor may be applied to the tissue in any order.

In embodiments, the fastener is a surgical staple or clip. In embodiments, the reactive members of a specific binding pair may include click chemistry functionality.

Kits are also described which include the surface activated surgical fastener, a fastening device, and a container which includes the functionalized liquid precursor.

DETAILED DESCRIPTION

Figure 1A:
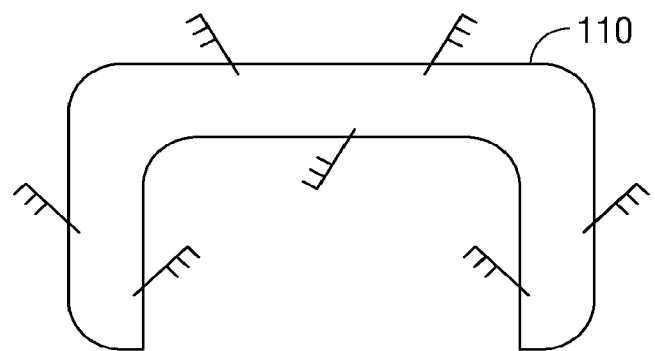
FIG. 1A schematically illustrates a surgical fastener in accordance with an embodiment described herein.

A surgical bonding system is provided which covalently bonds reactive members of a specific binding pair to one another via click chemistry. Click chemistry refers to a collection of reactive members having a high chemical potential energy capable of producing highly selective, high yield reactions. The reactive members react to form extremely reliable molecular connections in most solvents, including physiologic fluids, and often do not interfere with other reagents and reactions. Examples of click chemistry reactions include Huisgen cycloaddition, Diels-Alder reactions, thiol-alkene reactions, and maleimide-thiol reactions.

Huisgen cycloaddition is the reaction of a dipolarophile with a 1,3-dipolar compound that leads to 5-membered (hetero)cycles. Examples of dipolarophiles are alkenes and alkynes and molecules that possess related heteroatom functional groups (such as carbonyls and nitriles). 1,3-Dipolar compounds contain one or more heteroatoms and can be described as having at least one mesomeric structure that represents a charged dipole. They include nitril oxides, azides, and diazoalkanes. Metal catalyzed click chemistry is an extremely efficient variant of the Huisgen 1,3-dipolar cycloaddition reaction between alkyl-aryly-sulfonyl azides, C-N triple bonds and C-C triple bonds which is well-suited herein. The results of these reactions are 1,2 oxazoles, 1,2,3 triazoles or tetrazoles. For example, 1,2,3 triazoles are formed by a copper catalyzed Huisgen reaction between alkynes and alkyl/aryl azides. Metal catalyzed Huisgen reactions proceed at ambient temperature, are not sensitive to solvents, i.e., nonpolar, polar, semipolar, and are highly tolerant of functional groups. Non-metal Huisgen reactions (also referred to as strain promoted cycloaddition) involving use of a substituted cyclooctyne, which possesses ring strain and electron-withdrawing substituents such as fluorine, that together promote a [3+2] dipolar cycloaddition with azides are especially well-suited for use herein due to low toxicity as compared to the metal catalyzed reactions. Examples include DIFO and DIMAC. Reaction of the alkynes and azides is very specific and essentially inert against the chemical environment of biological tissues. One reaction scheme may be represented as:

a)

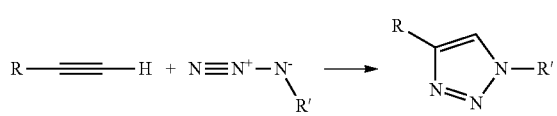

where R and R' are a polymeric material or a component of a biologic tissue.

The Diels-Alder reaction combines a diene (a molecule with two alternating double bonds) and a dienophile (an alkene) to make rings and bicyclic compounds.
Examples Include:
Dienes

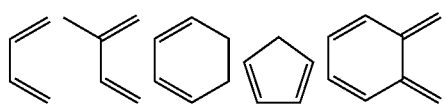

Dienophiles

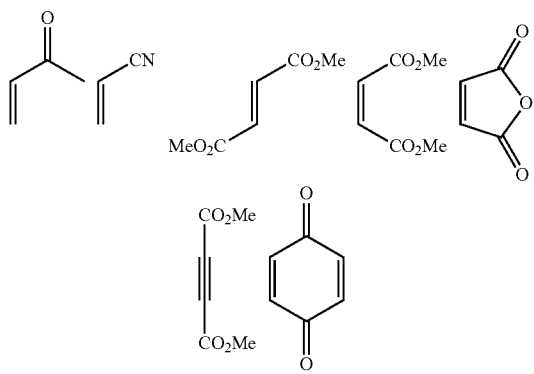

The thiol-alkene (thiol-ene) reaction is a hydrothiolation, i.e., addition of RS-H across a C=C bond. The thiol-ene reaction proceeds via a free-radical chain mechanism. Initiation occurs by radical formation upon UV excitation of a photoinitiator or the thiol itself. Thiol-ene systems form ground state charge transfer complexes and therefore photopolymerize even in the absence of initiators in reasonable polymerization times. However, the addition of UV light increases the speed at which the reaction proceeds. The wavelength of the light can be modulated as needed, depending upon the size and nature of the constituents attached to the thiol or alkene. A general thiol-ene coupling reaction mechanism is represented below:
Initiation

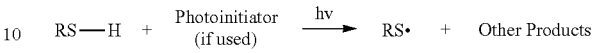

Propagation

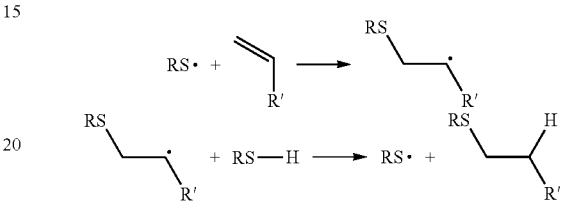

Termination

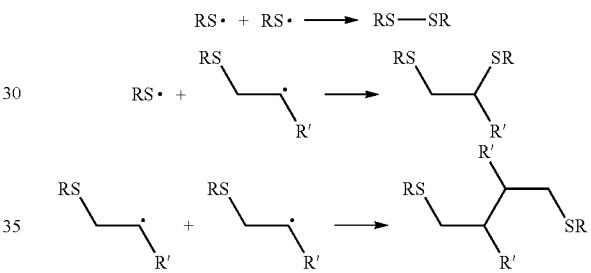

In accordance with the disclosure herein, a surgical fastener, such as a surgical staple is provided with a plurality of reactive members of a specific binding pair attached on the surface of the surgical fastener. When the reactive members of the surgical fastener are contacted with a tissue containing complementary reactive members of the specific binding pair, covalent attachment occurs, thus adhering the fastener to the tissue. In embodiments, the reactive members may be either a dipolarophile or a 1,3 dipolar compound depending on which complement is applied to the target tissue or the surgical fastener. For example, if a dipolarphile is located on the fastener, the 1,3 dipolar compound will be located on the tissue. If a dipolarphile is located on the tissue, the 1,3 dipolar compound will be located on the fastener. In embodiments, the Diels-Alder members of a specific binding pair may be either a diene or a dienophile depending on which complement is applied to the target tissue or the surgical fastener. For example, if a diene is located on the fastener, the dienophile can be located on the tissue. If a diene is located on the tissue, the dienophile can be located on the fastener. In embodiments, the thiol-ene members of a specific binding pair may be either a thiol and an alkene depending on which complement is applied to the target tissue or the fastener. For example, if a thiol is located on the fastener, the alkene can be located on the tissue. If a thiol is located on the tissue, the alkene can be located on the fastener.

The surgical fastener may be constructed from any biocompatible material including biocompatible non-absorbable metals, biocompatible absorbable metals, biocompatible absorbable polymers, biocompatible non-absorbable polymers and any combination thereof. Examples of suitable metals include titanium, stainless steel, nickel, zinc, magnesium, aluminum, copper, silver, gold, and combinations thereof. Alloys of any of these metals, such as steel alloys, titanium alloys, nickel chromium alloy, nickel/cobalt/chrome, copper-zinc-aluminum-nickel alloys, copper-aluminum-nickel alloys, zinc-copper-gold-iron alloys, and nickel-titanium (NiTi) alloys may also be used.

Examples of suitable polymers include polycarbonates, polyolefins, polymethacrylates, polystyrenes, polyamides, polyurethanes, polyethylene terephthalate, poly (lactic acid), poly (glycolic acid), poly (hydroxbutyrate), dioxanones (e.g., 1,4-dioxanone), δ-valerolactone, 1,dioxepanones (e.g., 1,4-dioxepan-2-one and 1,5-dioxepan-2-one), poly (phosphazine), polyesters, polyethylene glycol, polyethylene oxides, polyacrylamides, cellulose esters, fluoropolymers, vinyl polymers, silk, collagen, alginate, chitin, chitosan, hyaluronic acid, chondroitin sulfate, glycosaminoglycans, polyhydroxyethylmethylacrylate, polyvinylpyrrolidone, polyvinyl alcohol, polyacrylic acid, polyacetate, polycaprolactone, polypropylene, glycerols, poly(amino acids), copoly (ether-esters), polyalkylene oxalates, polyamides, poly (iminocarbonates), polyalkylene oxalates, polyoxaesters, polyorthoesters, polyphosphazenes, polypeptides and copolymers, block copolymers, homoploymers, blends and combinations thereof.

In the present application, the term "bioresorbable" and "bioabsorbable" are used interchangeably and are intended to mean the characteristic according to which an implant and/or a material is resorbed by the biological tissues and the surrounding fluids and disappears in vivo after a given period of time, that may vary, for example, from one day to several months, depending on the chemical nature of the implant and/or of the material. Non bioresorbable or non-bioabsorbable material—also called permanent material—is not substantially resorbed by tissues and surrounding fluids, after 2 years and more, keeping in particular most (e.g., >80%) of their mechanical properties after such a time. The term "biocompatible" is intended to mean the characteristic according to which an implant and/or a material is well integrated by the biological tissues and the surrounding fluids without inducing excessive inflammation reaction around the bulk of the material or due to its degradation. The material should avoid also the formation of a fibrous capsule which usually results in the delay of the cellular integration of a porous implant.

Many of the above described examples of metals or polymers may not contain functional groups on their surface or in their molecules. In embodiments, the reactive members are attached to the surgical fastener by surface modification techniques such as physical vapor deposition, chemical vapor deposition, plasma polymerization, plasma treatments, coupling treatments, such as silane coupling treatments and acid sensitization. Surface activation of the surgical fastener can be achieved by acid or base hydrolysis, treatment by means of cold plasma, by chemical reactions or electromagnetic radiations.

Hydrolysis can be conducted in the presence of an aqueous solution of a base or an acid to accelerate surface reaction, inasmuch as excessively long processes of activation can induce a reduction in molecular weight and thus in the mechanical properties of the material. Suitable bases for obtaining watery solutions suited to the aim are, for example, strong alkalis, such as LiOH, $Ba(OH)_2$, $Mg(OH)_2$, NaOH, KOH, $Na_2 CO_3$, $Ca(OH)_2$ and the weak bases, such as for example $NH_4 OH$ and the ammines such as methylamine, ethylamine, diethylamine and dimethylamine. Acids suitable for surface hydrolysis treatments can be chosen, for example, from among HCl, $HClO_3$, $HClO_4$, $H_2 SO_3$, $H_2 SO_4$, $H_3 PO_3$, $H_3 PO_4$, HI, $HIO_3$, HBr, lactic acid, glycolic acid. Surface activation by means of hydrolysis can be conducted at temperatures preferably comprised between 0 degrees Celsius and the material softening temperature.

Plasma treatment can be carried out both in the presence of a reactive gas, for example air, Ar, $O_2$ with the formation of surface activation of oxygenate type, such as —OH, —CHO, —COOH.

Surface treatment, whether hydrolytic or with plasma, can remain unaltered or can be followed by further chemical modifications to provide the first reactive groups on the bioabsorbable polymeric substrate. Thus, for example, the COONa groups generated by a base hydrolysis can be subsequently converted into COOH groups by treatment with strong mineral acids. Further, the surface freeing of alcoholic groups by means of a hydrolysis process can be followed by reaction by means of the addition of a compound provided with functional group or groups able to react with surface alcoholic groups, such as for example by means of the addition of an anhydride such as succinic anhydride, with the conversion of —OH groups into —O—CO—$CH_2$—$CH_2$—COOH groups. Suitable surface activation techniques are disclosed in U.S. Pat. No. 6,107,453, the entire disclosure of which is incorporated herein by this reference.

During manufacture of polymers, pendant functional groups can be incorporated into the polymer backbone by, e.g., copolymerization with functionalized monomer such as lactones, cyclic carbonates and morpholine-2,5-diones. The azido group, $N_3$ is a nucleophilic group that will exchange with other nucleophilic groups, e.g., —OH, —$NH_2$ and halogens (Br, Cl, or I). For example, 1,3-dipolar compounds may be conjugated to aliphatic polyesters, by copolymerizing ε-caprolactone and α-chloro-ε-caprolactone and then substituting an azide group for the Cl atom. Polyesters can incorporate pendant dipolarophiles, e.g., propargyl groups, by copolymerization of ε-caprolactone and α-propargyl-δ-valerolactone. Copolymers of L-lactide containing propargyl groups may, e.g., be prepared by ring opening copolymerization of 5-methyl-5-propargyloxycarbonyl-1,3-dioxanone with L-lactide at a molar ratio of about 90:10 with $ZnEt_2$ as a catalyst. See, Shi et al., Biomaterials, 29 (2008) 1118-1126. Azide functionalized polystyrene is synthesized using atom transfer radical polymerization and subsequent modification with azidotrimethylsilane and tetrabutylammonium fluoride. Sec, Dirks, et al., Chem. Comm., (2005) 4172-4174. Azides may be incorporated onto methacrylates, e.g., 3 azidopropyl methacrylate which is copolymerized to a block copolymer. Diels-Alder functionalities and thiol-ene functionalities are likewise incorporated into polymers herein.

Methods and devices according to the present disclosure may be used for closing wounds in virtually any body tissue, and may be particularly useful for closing wounds in the tissue of fragile body organs, such as lungs, stomach, liver, spleen, intestines, colon, and the like. The wounds may result from accidental trauma, surgical intervention, or virtually any other cause, with the methods and devices being particularly useful for the closure of surgical resections made in the lungs (lung volume reductions, bullectomies, lobectomies, segmentectomies, bronchial resections, wedge resections, pneumonectomies, pneumoreductions, etc.), in the gastrointestinal tract, (gastrectomies, intestinal/colon resection/polypectomy), in the liver, and in the spleen. The use of a surgical fastener and a liquid precursor, each having a plurality of different complimentary reactive members of a specific binding pair as described herein, provides the wound with both secure mechanical closure of the wound and prevention or inhibition of fluid leakage, including both air leakage and liquid fluid leakage, such as blood and other bodily fluids.

The surgical fasteners described herein are meant to include any conventional surgical fasteners used for closing of a wound. Exemplary fasteners include sutures, staples, clips, pins, hooks, screws, cables, anchors, and the like. In embodiments, the surgical fastener may be a surgical staple. In embodiments, the fastener may be a surgical clip. The surgical staple or clip may be selected from any conventional staple type that is suitable for use in closing biologic tissue, e.g., wound closure, or wound repair. Many types of staples are currently available and are well known to those skilled in the art. Exemplary staples may be made from materials which include polyglycolic acid, polylactic acid, polycaprolactone, poly(esteramides), polydioxanone, polycarbonates, polyesters, nylons, polyethylenes, polypropylenes, ultra-high molecular weight polyethylenes, polysulfones, polytetrafluroethylene (PTFE), stainless steel, titanium, nitinol, absorbable metals, such as magnesium based alloys and the like. Any of the biocompatible materials listed above may be utilized.

In certain embodiments, the fasteners may be formed from one or more bioresorbable, natural biological polymers. Suitable natural biological polymers include, but are not limited to, collagen, gelatin, cellulose, hydroxypropyl cellulose, carboxyethyl cellulose, chitin, chitosan, hyaluronic acid, chondroitin sulfate and other glycosaminoglycan and combinations thereof. In alternate embodiments, the polymer constituent may be a polysaccharide such as chitin or chitosan, or polysaccharides modified by oxidation of alcohol functions into carboxylic functions such as oxidized cellulose. It is contemplated that the natural biological polymers may be combined with any biocompatible synthetic materials to produce the fastener.

Indeed, the staple or clip may be produced from fibers of any biocompatible polymer using any techniques known to those skilled in the art, such as extruding, molding, spinning, knitting, weaving, tatting, braiding, non-woven techniques, solvent casting and the like. It is envisioned that the staple or clip may be formed into any shape, design and/or configuration suitable for mechanically closing a wound. In addition, the surgical fastener may be able transition from an original configuration to a wound closing configuration. For example, U.S. Pat. No. 4,407,286, discloses a method wherein a staple transitions from having generally straight staple legs to a staple in which the staple legs are bent by the anvil of the stapler upon implantation into the wound tissue. The bending or deformation of the staple legs are intended to further anchor the fastener into the tissue and thereby close the wound more securely. Of course, the fasteners described herein may transition into any shape suitable for closing the wound and many other configurations may be known to those skilled in the art.

In embodiments, the fastener is a staple. The staples described herein may be designed to be used with any suitable surgical stapling device. Some non-limiting examples of suitable surgical stapling devices include linear staplers, annular staplers, end-to-end anastomosis staplers, and surgical staplers capable of delivering a fluid to the site of implantation. The surgical stapling devices employed may also be designed to simultaneously cut and seal an extended segment of tissue in a patient, thus vastly reducing the time and risks of such procedures.

Linear or annular surgical stapling devices may be employed by surgeons to sequentially or simultaneously apply one or more linear rows of surgical fasteners, e.g., staples, or two-part fasteners, to body tissue for the purpose of joining segments of body tissue together and/or for the creation of anastomosis. Linear surgical stapling devices generally include a pair of jaws or finger-like structures between which body tissue to be joined is placed. When the surgical stapling device is actuated and/or "fired," firing bars move longitudinally and contact staple drive members in one of the jaws, and surgical staples are pushed through the body tissue and into/against an anvil in the opposite jaw thereby crimping the staples closed. A knife blade may be provided to cut between the rows/lines of staples. Examples of such linear surgical stapling devices are described in U.S. Pat. Nos. 5,465,896; 6,330,965; and 6,817,508, the entire content of each of which are incorporated herein by reference.

Annular surgical stapling devices generally include an annular staple cartridge assembly including a plurality of annular rows of staples, typically two, an anvil assembly operatively associated with the annular cartridge assembly, and an annular blade disposed internal of the rows of staples.

An end-to-end anastomosis stapler typically places an array of staples into the approximated sections of a patient's bowels or other tubular organs. The resulting anastomosis contains an inverted section of bowel which contains numerous "B" shaped staples to maintain a secure connection between the approximated sections of bowel. An example of such a stapler is disclosed in U.S. Pat. No. 5,392,979, the entire content of which is incorporated herein by reference.

Some surgical staplers include the ability to deliver a liquid or fluid to the site of implantation of the staple. An example of such a stapler is disclosed in U.S. Pat. No. 7,431,730, the entire content of which is incorporated herein by reference. In such cases, the liquid precursors described herein may be carried by the stapler and applied to the tissue before, after or during the firing of the stapler. Thus in some embodiments, the stapler may apply both the surgical fastener and the liquid precursor simultaneously.

The surgical fasteners described herein are intended to be implanted into biological tissue which includes reactive members of a specific binding pair which are complimentary to the reactive members on the surface of the fasteners. By complimentary, the reactive members on the surgical fasteners are able to form a chemical bond with the reactive members of positioned on the biological tissue.

Biological tissue is provided with reactive members of a specific binding pair by conjugation to various components of tissue such as proteins, lipids, oligosaccharides, oligonucleotides, glycans, including glycosaminoglycans. In one embodiment, the reactive members or complementary reactive members are attached directly to components of the tissue. In another embodiment, the reactive members or complementary reactive members are attached to components of the tissue via a linker. In either case, situating the reactive members or complementary reactive members on the tissue can be accomplished by forming a liquid precursor which includes the reactive members or complementary reactive members and applying the liquid precursor to the tissue at anytime before, during or after the implantation of the surgical fastener.

The liquid precursor may be a solution, suspension, emulsion, or dispersion which includes the reactive members complimentary to the reactive members on the fastener.

The precursor may further include any solvent suitable for carrying the appropriate reactive members, as well as any biocompatible or bioactive material described herein. The liquid precursor may be poured, sprayed, wiped, brushed, rolled, dipped, atomized, or painted onto the tissue, whereupon the reactive members or complementary reactive members are incorporated into or onto the tissue.

1,3-Dipolar compounds can be incorporated into proteins, lipids, oligosaccharides, oligonucleotides and glycans using, e.g., metabolic machinery, covalent inhibitors and enzymatic transfers. For example, an azido group, $N_3$, can be applied at the N-terminus of proteins or peptides using azidoacetyl chloride. See, e.g., Haridas, et al., Tetrahedron Letters 48 (2007) 4719-4722. The azido group is a nucleophilic group that will exchange with other nucleophilic groups, e.g., —OH, —$NH_2$ and halogens (Br, Cl, or I). $NaN_3$ is an azidizing agent which is capable of aziding proteins by simply contacting the proteins with a 10 times molar excess of $NaN_3$. A process for C-terminal azidization is described in Cazalis, et al., Bioconjugate Chem., 15 (2004) 1005-1009. Incubation of cells with peracetylated N-azidoacetylmannosamine provides cell surface glycans with azido sialic acid. See, e.g., Codelli et al., J. Amer. Chem. Soc., 130 (34) 11486-11493 (2008). Azido-tagged lipids are described in Smith, et al., Bioconjugate Chem., 19 (9), 1855-1863 (2008). PEGylation is a commonly used technique for adding groups to peptides and proteins and is suitable for use herein. For example, PEG may be covalently bound to amino acid residues via a reactive group. Reactive groups (as opposed to reactive members herein) are those to which an activated PEG molecule may be bound (e. g., a free amino or carboxyl group). For example, N-terminal amino acid residues and lysine (K) residues have a free amino group and C-terminal amino acid residues have a free carboxyl group. Sulfhydryl groups (e.g., as found on cysteine residues) may also be used as a reactive group for attaching PEG. In addition, enzyme-assisted methods for introducing activated groups (e.g., hydrazide, aldehyde, and aromatic-amino groups) specifically at the C-terminus of a polypeptide. Accordingly, PEG incorporating 1,3-dipolar compounds may be utilized herein. Those skilled in the art can utilize any known process for coupling a 1,3-dipolar compound into proteins, lipids, oligosaccharides, oligonucleotides and glycans.

Dipolarophile functionalized proteins and peptides can be synthesized by linking at the N-terminus with, for example, an alkyne (e.g., 3 butynyl chloroformate), in connection with a tripeptide (GlyGlyArg). See, Dirks, et al., supra. A suitable tripeptide herein is the well-known cell adhesion sequence RGD. It should be understood that, as used herein, "proteins" is intended to encompass peptides and polypeptides. In one embodiment, thiols on cysteines are functionalized with alkyne bearing maleimide. Id. Providing a C-terminal dipolarophile can be accomplished, e.g., by coupling with propargylamine using a cross-linking agent such as N-hydroxysuccinimide/DCC. See, e.g., Haridas, et al. supra. Terminal alkynes can be installed using metabolic building blocks such as alkynoic acids. Lipids may be functionalized with alkynes. For example, alkyne modified fatty acids can be generated by reaction of terminal alkynyl-alkyl bromide with trimethyl phosphine to yield a 16 carbon alkynyl-dimethylphosphonate. See, e.g., Raghavan et al., Bioorg. Med. Chem. Lett., 18 (2008) 5982-5986. As above, PEGylation may be used for adding dipolarophile groups to peptides and proteins and is suitable for use herein. Diels-Alder functionalities and thiol-ene functionalities are likewise attached to proteins, lipids, oligosaccharides, oligonucleotides and glycans.

The reactive members or complementary reactive members may be also attached to biological tissue via a linker. In certain embodiments, the linker is or includes a ligand which bears a reactive member. The ligand binds to a desired target on the tissue and thus provides a vehicle for transporting and indirectly binding the reactive member to the tissue. The ligand herein is any molecule or combination of molecules which demonstrates an affinity for a target. Examples of ligands include nucleic acid probes, antibodies, hapten conjugates, and cell adhesion peptides such as RGD. The mechanisms involved in obtaining and using such ligands are well-known. In embodiments, reactive members or complementary reactive members are incorporated into saccharides or polysaccharides and metabolically incorporated into cells. See, e.g., Baskin et al., supra.

Antibodies that specifically recognize antigens are useful in accordance with one embodiment herein. Antibodies which are conjugated to a reactive member are utilized to bind to proteins located on tissue. Monoclonal or polyclonal antibodies are raised against an antigen which can be any component of biological tissue and then purified using conventional techniques. The term "antibody" is intended to include whole antibodies, e.g., of any isotype (IgG, IgA, IgM, IgE, etc.), and to include fragments thereof which arc also specifically reactive with a vertebrate, e.g., mammalian, protein. Antibodies may be fragmented using conventional techniques and the fragments screened for utility in the same manner as for whole antibodies. Thus, the term includes segments of proteolytically-cleaved or recombinantly-prepared portions of an antibody molecule that are capable of selectively reacting with a certain protein. Non-limiting examples of such proteolytic and/or recombinant fragments include Fab, F(ab')2, Fab', Fv, and single chain antibodies (sev) containing a V[L] and/or V[H] domain joined by a peptide linker. The scFv's may be covalently or non-covalently linked to form antibodies having two or more binding sites. The present disclosure includes polyclonal, monoclonal or other purified preparations of antibodies and recombinant antibodies.

After purification, the ligands (e.g., antibodies, nucleic acid probes, hapten conjugates and cell adhesion peptides), are conjugated or linked to reactive members or complementary reactive members in the manners described above. In addition, reactive members or complementary reactive members can be linked to ligands by cross-linking procedures which, in accordance with the present invention, do not cause denaturing or misfolding of the ligands. The terms "linked" or "conjugated" as used herein are used interchangeably and are intended to include any or all of the mechanisms known in the art for coupling the reactive members or complementary reactive members to the ligand. For example, any chemical or enzymatic linkage known to those with skill in the art is contemplated including those which result from photoactivation and the like. Homofunctional and heterobifunctional cross linkers are all suitable. Reactive groups (distinguishable from reactive members or complementary reactive members herein) which can be cross-linked with a cross-linker include primary amines, sulfhydryls, carbonyls, carbohydrates and carboxylic acids.

Cross-linkers are conventionally available with varying lengths of spacer arms or bridges. Cross-linkers suitable for reacting with primary amines include homobifunctional cross-linkers such as imidoesters and N-hydroxysuccinimidyl (NHS) esters. Examples of imidoester cross-linkers include dimethyladipimidate, dimethylpimelimidate, and dimethylsuberimidate. Examples of NHS-ester cross-linkers include disuccinimidyl glutamate, disuccinimidyl suberate and bis (sulfosuccinimidyl) suberate. Accessible amine groups present on the N-termini of peptides react with NHS-esters to form amides. NHS-ester cross-linking reactions can be conducted in phosphate, bicarbonate/carbonate, HEPES and borate buffers. Other buffers can be used if they do not contain primary amines. The reaction of NHS-esters with primary amines should be conducted at a pH of between about 7 and about 9 and a temperature between about 4° C. and 30° C. for about 30 minutes to about 2 hours. The concentration of NHS-ester cross-linker can vary from about 0.1 to about 10 mM. NHS-esters are either hydrophilic or hydrophobic. Hydrophilic NHS-esters are reacted in aqueous solutions although DMSO may be included to achieve greater solubility. Hydrophobic NHS-esters are dissolved in a water miscible organic solvent and then added to the aqueous reaction mixture.

Sulfhydryl reactive cross-linkers include maleimides, alkyl halides, aryl halides and a-haloacyls which react with sulfhydryls to form thiol ether bonds and pyridyl disulfides which react with sulfhydryls to produce mixed disulfides. Sulfhydryl groups on peptides and proteins can be generated by techniques known to those with skill in the art, e.g., by reduction of disulfide bonds or addition by reaction with primary amines using 2-iminothiolane. Examples of maleimide cross-linkers include succinimidyl 4-{N-maleimido-methyl) cyclohexane-1-carboxylate and m-maleimidobenzoyl-N-hydroxysuccinimide ester. Examples of haloacetal cross-linkers include N-succinimidyl (4-iodoacetal) aminobenzoate and sulfosuccinimidyl (4-iodoacetal) aminobenzoate. Examples of pyridyl disulfide cross-linkers include 1,4-Di-[3'-2'-pyridyldithio(propionamido)butane] and N-succinimidyl-3-(2-pyridyldithio)-propionate.

Carboxyl groups are cross-linked to primary amines or hydrazides by using carbodimides which result in formation of amide or hydrazone bonds. In this manner, carboxy-termini of peptides or proteins can be linked. Examples of carbodiimide cross-linkers include 1-ethyl-3-(3-dimethyl-aminopropyl)-carbodiimide hydrochloride and N, $N^1$-dicyclohexylcarbodiimide. Arylazide cross-linkers become reactive when exposed to ultraviolet radiation and form aryl nitrene. Examples of arylazide cross-linkers include azidobenzoyl hydrazide and N-5-azido-2 nitrobenzoyloxysuccinimide. Glyoxal cross linkers target the guanidyl portion of arginine. An example of a glyoxal cross-linker is p-azidophenyl glyoxal monohydrate.

Heterobifunctional cross-linkers which possess two or more different reactive groups are suitable for use herein. Examples include cross-linkers which are amine-reactive at one end and sulfliydryl-reactive at the other end such as 4-succinimidyl-oxycarbonyl-a-(2-pyridyldithio)-toluene, N-succinimidyl-3-(2-pyridyldithio)-propionate and the maleimide cross-linkers discussed above.

Attachment of reactive members to the surgical fastener functionalizes the device such that upon exposure to their complementary reactive members which are situated on tissue, they are activated and form a covalent bond, thus adhering the device to the tissue. In one embodiment, a linker between the product of the reactive members or complementary reactive members and the biological tissue is degradable by, e.g., hydrolysis or enzymatic action. In this manner, the surgical fastener can be removable after a period of time. The degradable linkage may be, e.g., chelates or chemically or enzymatically hydrolyzable or absorbable. Illustrative chemically hydrolyzable degradable linkages include polymers, copolymers and oligomers of glycolide, dl-lactide, 1-lactide, caprolactone, dioxanone, and tritnethylene carbonate. Illustrative enzymatically hydrolyzable biodegradable linkages include peptidic linkages cleavable by metalloproteinases and collagenases. Additional illustrative degradable linkages include polymers and copolymers of poly(hydroxy acid)s, poly(orthocarbonate)s, poly(anhydride)s, poly(lactone)s, poly(amino acid)s, poly(carbonate)s, poly(saccharide)s and poly(phosphonate)s. In certain embodiments, the degradable linkage may contain ester linkages. Some non-limiting examples include esters of succinic acid, glutaric acid, propionic acid, adipic acid, or amino acids, as well as carboxymethyl esters.

The surgical fastener may be cut to a desired shape, packaged in single or dual pouches and sterilized by gamma or beta irradiation at 25-35 Kgy or by ethylene oxide. The liquid precursor may be sterilized by the previous cited method or by filtration under sterile conditions by 0. 22 um filter.

In some embodiments, at least one bioactive agent may be combined with the fasteners and/or the liquid precursors described herein. For example, a bioactive agent may be combined with the polymer used to form the fastener, and/or a bioactive agent may be coated onto any portion of the fastener. The at least one agent may be freely released by the fastener or may be chemically bound to the surface of the suture.

The term "bioactive agent", as used herein, is used in its broadest sense and includes any substance or mixture of substances that have clinical use. Consequently, bioactive agents may or may not have pharmacological activity per se, e.g., a dye, or fragrance. Alternatively a bioactive agent could be any agent which provides a therapeutic or prophylactic effect, a compound that affects or participates in tissue growth, cell growth, cell differentiation, an anti-adhesive compound, a compound that may be able to invoke a biological action such as an immune response, a compound that adds lubricity to the outer surface of the fastener, or could play any other role in one or more biological processes. It is envisioned that the bioactive agent may be applied to the present fastener materials in any suitable form of matter, e.g., films, powders, liquids, gels and the like.

Examples of classes of bioactive agents which may be utilized in accordance with the present disclosure include anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, lubricants, oils, and enzymes. It is also intended that combinations of bioactive agents may be used.

Suitable antimicrobial agents which may be included as a bioactive agent in the fastener materials of the present disclosure include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B and antimicrobial polysaccharides such as fucans and derivatives may be included as a bioactive agent in the fasteners of the present disclosure.

Other bioactive agents which may be included as a bioactive agent in the fasteners in accordance with the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; antiparkinson agents such as L-dopa; anti-spasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fungals; anti-virals; anticoagulants; anticonvulsants; antidepressants; antihistamines; and immunological agents.

Other examples of suitable bioactive agents which may be included in the present fastener materials include viruses and cells, peptides, polypeptides and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons ((3-IFN, (a-IFN and y-IFN), erythropoietin, nucleases, tumor necrosis factor, colony stimulating factors (e.g., GCSF, GM-CSF, MCSF), insulin, anti-tumor agents and tumor suppressors, blood proteins, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); protein inhibitors, protein antagonists, and protein agonists; nucleic acids, such as antisense molecules, DNA and RNA; oligonucleotides; polynucleotides; and ribozymes.

Figure 1B:
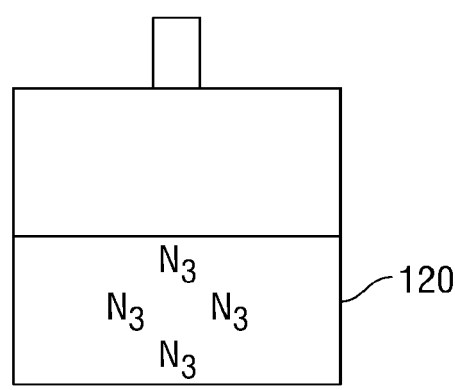
FIG. 1B schematically illustrates a liquid precursor in accordance with an embodiment described herein.

Turning now to FIGS. 1A and 1B, surgical fastener 110 and liquid precursor 120 are shown, respectively. Surgical fastener 110, made from a biocompatible material, is schematically shown as a staple having at least a portion of the staple surface functionalized with a plurality of first reactive members, e.g., alkyne groups in this instance. Liquid precursor 120 is schematically shown as a solution which includes a plurality of second complimentary reactive members, e.g., azide groups. As depicted in FIGS. 1A-1B, the specific binding pairs may include first reactive members which are alkynes and second reactive members as azides. Of course, the first and second reactive members are not meant to be limited to these two specific reactive members, however for purposes of clarity the azide/alkyne complimentary reactive members have been added to the figures.

Figure 2A:
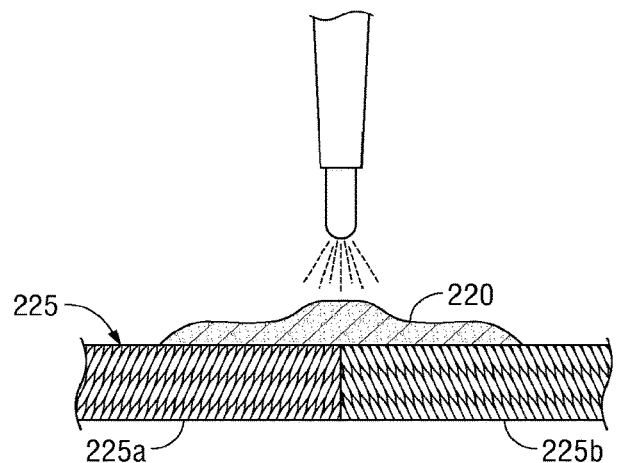
FIGS. 2A through 2C schematically illustrate a method of closing a wound in accordance with an embodiment described herein.
Figure 2B:
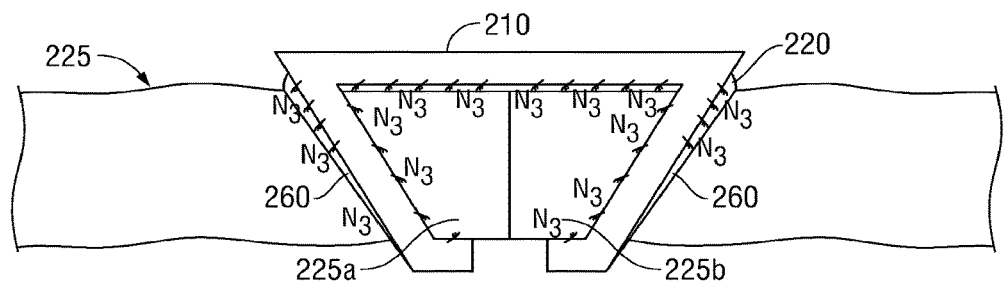
Figure 2C:
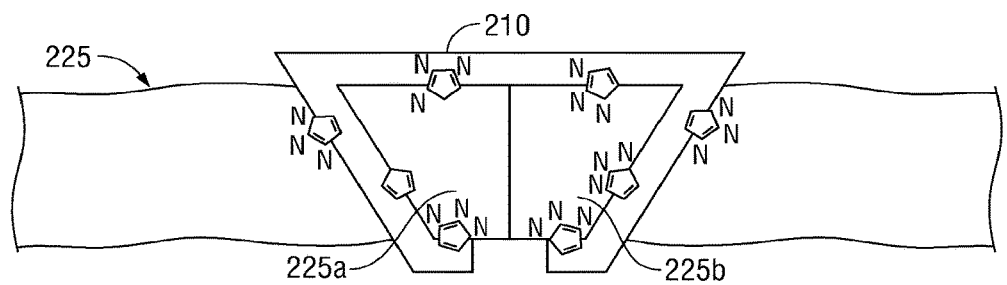

As schematically shown in FIGS. 2A-2C, methods of closing wounds may include the steps of applying or wetting first and second approximated portions 225a, 225b of wound tissue 225 with liquid precursor 220 and contacting wetted wound tissue 225 with surgical fastener 210 to mechanically close the wound tissue. Liquid precursor is functionalized to include reactive members, e.g., azide groups which are complimentary to the reactive members on the surface of surgical fastener 210. In this embodiment, surgical fastener 210 is shown as a staple which is surface activated to include reactive alkyne members.

As depicted in FIG. 2B, gaps 260 between fastener 210 and tissue 225 may occur during the implantation of fastener 210. Under previous conditions, gaps 260 might allow for the wound to leak bodily fluids, weaken the strength of the mechanical wound closure device and/or promote microbial growth which may lead to infections. However, in accordance with the methods described herein, liquid precursor will seal a portion of the wound and functionalize tissue 225 with reactive members which are complimentary to the reactive members on fastener 210. As schematically shown, tissue 225 will include azide functionality and fastener 210 will include alkyne functionality.

After the fastener has contacted the functionalized liquid precursor or tissue, the complimentary reactive members will be positioned next to each other and in close proximity to allow for the complimentary members to react and form a chemical bond. As those skilled in the art will recognize, reaction times between the azide and alkyne members can be reduced from about 24 hours at room temperature to mere seconds at room temperature by the presence of transition metal ions, such as copper ions.

As schematically shown in FIG. 2C, following interaction between the complimentary reactive members, at least portions of fastener 210 is covalently bound to at least portions of tissue 225 via triazole linkages. This chemical bond increases the mechanical strength of the fastener and creates a seal about the wound and the fastener which may prevent leakage of bodily fluids from the wound.

In some embodiments, methods of closing wounds may include the steps of contacting wound tissue 225 with surgical fastener 210 to mechanically close the wound and applying or wetting wound tissue 225 with liquid precursor 220.

In still other embodiments, a method of closing a wound may include the step of simultaneously wetting wound tissue 225 with a liquid precursor 220 and contacting wound tissue 225 with surgical fastener 210 to mechanically close the wound.

A kit for closing wounds is also described herein which includes a surgical fastener such as a staple or clip which has a plurality of reactive members of a specific binding pair attached to a surface of the fastener and a container which optionally functions as an applicator and is adapted to contain a mixture including complementary reactive members of the specific binding pair, the complementary reactive members having a functionality that will adhere them to biological tissue upon contact. The kit may optionally include a surgical fastener delivery device, such as a clip applier, surgical stapler, knot-pusher, surgical drill for implanting screws and the like. The kit may also optionally include a container which contains a catalyst for causing the reactive members of a specific binding pair to bind with the complementary reactive members of the specific binding pair. The catalyst may be a metal such as copper in solution. In embodiments, the kit contains a generator of microwaves or ultraviolet radiation.

It should be understood that variations can be made to the above embodiments that are with the purview of ordinary skill in the art. For example, other click chemistry reactions are suitable for use herein, e.g., Staudinger reaction of phosphines with alkyl azides. It is contemplated that the above-described cross-linkers may be applied to polymers which make up the surgical fastener to bind reactive members or complementary reactive members thereto. Accordingly, those skilled in the art can envision modifications which are included within the scope of the claimed invention that are not expressly set forth herein.

What is claimed is:

1. A kit comprising a polymeric surgical fastener having a functionalized surface including a plurality of reactive members of a specific binding pair and a container containing a liquid precursor including complementary reactive members of the specific binding pair, wherein upon interaction the reactive members and the complementary reactive members can bind to one another to form covalent bonds and the polymeric surgical fastener is selected from the group consisting of sutures, staples, clips, pins, hooks, screws, cables, and anchors.

2. A kit according to claim 1 further comprising a second container for containing a catalyst.

3. A kit according to claim 2 wherein the catalyst is a metal.

4. A kit according to claim 3 wherein the metal is a copper solution.

5. A kit according to claim 1 further comprising a device for delivering the liquid precursor to tissue.

6. A kit according to claim 5 wherein the device for delivering the liquid precursor to the tissue is a sprayer.

7. A kit according to claim 1 further comprising generator for generating microwaves or ultraviolet radiation.

8. A kit according to claim 1 wherein the surgical fastener comprises a staple.

9. A kit according to claim 1 further comprising a delivery device adapted to implant the surgical fastener.

10. The kit according to claim 9 wherein the delivery device is a surgical stapling device.

11. A kit according to claim 1 wherein the members of the specific binding pair bind to one another via a reaction selected from the group consisting of Huisgen cycloaddition reaction, a Diels-Alder reaction and a thiol-ene reaction.

12. A kit according to claim 11 wherein the reaction is catalyzed by copper to activate an alkyne and an azide for [3+2] cycloaddition.

13. A kit according to claim 11 wherein the reaction involves a cyclooctyne reagent and an azide for [3+2] cycloaddition.

14. A kit according to claim 1 wherein the members of the specific binding pair are alkynes and azides.

15. A kit according to claim 1 wherein the members of the specific binding pair are thiols and alkenes.

16. A kit according to claim 1 wherein the members of the specific binding pair are dienes and alkenes.

17. A kit according to claim 1 wherein the complementary reactive members of the liquid precursor are conjugated to a linker adapted to link the complementary reactive members to tissue.

18. A kit according to claim 17 wherein the complementary reactive members are linked to the tissue via an RGD linker.

19. A kit according to claim 17 wherein the complementary reactive members are conjugated to a linker selected from the group consisting of antibody, Fab, F(ab')$_2$, Fv, single chain antibody (SCA) and single complementary-determining region (CDR).

20. A kit according to claim 1 wherein the surgical fastener is provided with the reactive members of the specific binding pair by surface modification techniques selected from the group consisting of physical vapor deposition, chemical vapor deposition, plasma treatments, coupling treatments, acid hydrolysis and base hydrolysis.

21. A kit according to claim 1 wherein the surgical fastener is made of a polymer selected from the group consisting of polycarbonates, polyolefins, polymethacrylates, polystyrenes, polyamides, polyurethanes, polyethylene terephthalate, poly(lactic acid), poly(glycolic acid), poly(hydroxbutyrate), dioxanones (e.g., 1,4-dioxanone), δ-valerolactone, 1,dioxepanones (e.g., 1,4-dioxepan-2-one and 1,5-dioxepan-2- one), poly(phosphazine), polyesters, polyethylene glycol, polyethylene oxides, polyacrylamides, cellulose esters, fluoropolymers, vinyl polymers, silk, collagen, alginate, chitin, chitosan, hyaluronic acid, chondroitin sulfate, polyhydroxyethylmethylacrylate, polyvinylpyrrolidone, polyvinyl alcohol, polyacrylic acid, polyacetate, polycaprolactone, polypropylene, glycerols, poly(amino acids), copoly(ether-esters), polyalkylene oxalates, polyamides, poly (iminocarbonates), polyalkylene oxalates, polyoxaesters, polyorthoesters, polyphosphazenes, polypeptides and copolymers, block copolymers, homopolymers, blends and combinations thereof.

22. A kit according to claim 1 wherein the liquid precursor further comprises a bioactive agent.

* * * * *